US009700386B2

(12) United States Patent
Horvath

(10) Patent No.: US 9,700,386 B2
(45) Date of Patent: Jul. 11, 2017

(54) IMPLANT FOR BONE DISTRACTION

(71) Applicant: CELGEN AG, Zug (CH)

(72) Inventor: Domonkos Horvath, Jestetten (DE)

(73) Assignee: CELGEN AG, Zug (CH)

( * ) Notice: Subject to any disclaimer, the term of this patent is extended or adjusted under 35 U.S.C. 154(b) by 65 days.

(21) Appl. No.: 14/649,842

(22) PCT Filed: Dec. 5, 2013

(86) PCT No.: PCT/EP2013/075634
§ 371 (c)(1),
(2) Date: Jun. 4, 2015

(87) PCT Pub. No.: WO2014/086910
PCT Pub. Date: Jun. 12, 2014

(65) Prior Publication Data
US 2015/0313689 A1 Nov. 5, 2015

(30) Foreign Application Priority Data
Dec. 5, 2012 (DE) .......................... 10 2012 024 205

(51) Int. Cl.
*A61C 8/00* (2006.01)
*A61C 8/02* (2006.01)
*A61B 17/86* (2006.01)
*A61B 17/66* (2006.01)

(52) U.S. Cl.
CPC .......... *A61C 8/0006* (2013.01); *A61B 17/666* (2013.01); *A61B 17/863* (2013.01); *A61C 8/0012* (2013.01); *A61C 8/0022* (2013.01); *A61C 8/0034* (2013.01); *A61C 8/0048* (2013.01); *A61C 2008/0084* (2013.01)

(58) Field of Classification Search
CPC ... A61C 8/0006; A61C 8/0022; A61C 8/0034; A61C 8/0048; A61C 8/0012; A61C 17/863; A61C 17/666
See application file for complete search history.

(56) References Cited

U.S. PATENT DOCUMENTS

| | | |
|---|---|---|
| 5,980,252 A | 11/1999 | Samchukov et al. |
| 6,270,346 B1 | 8/2001 | Grabenhofer et al. |
| 6,537,070 B1 | 3/2003 | Stucki-McCormick |
| 2005/0074437 A1 | 4/2005 | Horvath |

(Continued)

FOREIGN PATENT DOCUMENTS

| | | |
|---|---|---|
| DE | 19907420 A1 | 9/2000 |
| WO | WO-01/91663 A1 | 12/2001 |

(Continued)

OTHER PUBLICATIONS

Office Action regarding Application No. 13 799 578.3-1658, dated Jun. 14, 2016. Partial machine translation provided.

(Continued)

*Primary Examiner* — Glenn Richman
(74) *Attorney, Agent, or Firm* — Stephen T. Olson; Harness, Dickey & Pierce, P.L.C.

(57) ABSTRACT

An implant includes an implant body and a distraction membrane. The distraction membrane is connected to the implant by a connection element. The connection element is arranged movably at least over a portion of a longitudinal axis of the implant body such that the distraction membrane is slidable along at least a portion of the longitudinal axis of the implant body.

20 Claims, 10 Drawing Sheets

(56) References Cited

U.S. PATENT DOCUMENTS

2006/0058785 A1    3/2006  Fuchs et al.
2013/0261672 A1   10/2013  Horvath

FOREIGN PATENT DOCUMENTS

WO     WO-03/051220 A2    6/2003
WO     WO-2012/076160 A1  6/2012

OTHER PUBLICATIONS

International Search Report for PCT/EP2013/075634, ISA/EP, Rijswijk, NL, mailed Feb. 26, 2014.
English Translation of the International Preliminary Report on Patentability (Ch. II) for PCT/EP2013/075634, IPEA/EP, Rijswijk, NL, issued Mar. 24, 2015.

IMPLANT FOR BONE DISTRACTION

CROSS-REFERENCE TO RELATED APPLICATIONS

This application is a 371 U.S. National Stage of International Application No. PCT/EP2013/075634, filed on Dec. 5, 2013, which claims the benefit of and priority to German Patent Application No. 1020120242050, filed on Dec. 5, 2012. The disclosures of the above applications are incorporated herein by reference.

FIELD

The present invention relates to an implant, preferably a tooth implant, comprising an implant body and a distraction membrane, the use of the implant for callus distraction and a method for implanting same.

BACKGROUND

In order to set implants in a jaw permanently and firmly, the jawbone, at the appropriate point, has to be sufficiently wide and also strong enough. In other words, bone has to be present in sufficient quantity as well as quality.

If there is insufficient bone available for a secure anchoring of a sufficiently large or long implant, a so-called jawbone build-up must be provided. In such cases, increasing bone height is regarded as particularly problematic. Different methods are used for harvesting bone.

In case of a slight lack of bone width, the bone required for the jawbone build-up can be harvested during the operation. Bone replacement material can also be used or the additive amount can be extended by mixing bones and replacement material. This augmentation region is frequently protected with a flexible membrane, and so the bone can heal unimpeded. Further methods are bone spreading, bone splitting, bone block transplantation, sinus lift, cavity techniques, to some extent also with the use of bone replacement materials and protective membranes, and socket preservation.

From a biological point of view, an autologous spongiosa graft is the best replacement material for a bone. However, the availability of such grafts is limited and they show a high resorption rate after transplantation.

The materials and techniques used in the prior art frequently provide insufficient bone quality, and so implants are not securely anchored in their implant sockets. In addition, the bone replacement is frequently not sufficiently vascularized, which increases the risk of infection and affects the regeneration of the bone. In addition, growth factors are frequently used in methods from the prior art, which significantly increase the costs for the procedures.

Instead of using a bone replacement, missing bone substance can to some extent also be filled through bone regeneration. Segmental interruptions of the bony continuity on long bones can thus be treated by means of distraction osteogenesis.

Callus distraction has already been known for more than a hundred years. The most important biological stimulus for bone formation is mechanical load. It releases piezoelectric forces which activate osteoblasts and osteoclasts. Distraction osteogenesis induces the bone regeneration by triggering growths stimuli through slow separation of bone segments. With this method, distraction leads to the direct formation of woven bones. The defined tensile stress during bone generation is essential. If such a defined tensile stress is applied to bone fragments, the mesenchymal tissue in the gap and the adjoining fragment ends shows osteogenic potential. If sufficient vascular potency is present, progressive distraction results in metaplasia of the organized hematoma, also called blood coagulum, in a zone of longitudinally arranged, fibrous tissue which, under optimal external and internal conditions, can directly transform into woven bones. However, this is aggravated by the fact that the bone tissue is subject to a highly complex control during its regeneration.

WO 03/051220 A2 describes a method for distracting a jawbone by means of bone segments.

DE 10 2010 055 431 A1, WO 01/91663 A1, and U.S. Pat. No. 5,980,252 describe devices and methods for callus distraction by means of artificial interfaces, for example membranes. The membranes used in these methods are plane plates or platelets which in most cases are made of a metal, for example titanium. The membranes are moved by different devices and actuating elements, such as screws or wire rope hoists. These actuating elements are to some extent very complex or the lifting of the membrane can only be adjusted insufficiently. Furthermore, in order to move the membrane, the actuating element must frequently be anchored on adjacent teeth or in the bone. This leads to additional treatment or even surgical steps.

U.S. Pat. No. 6,537,070 B1 discloses a multipiece implant which is supposed to generate distraction osteogenesis by unscrewing the individual parts. However, this is at best limited to the direct region of the implant thread. A typical bone defect which affects the entire width of a tooth gap is thus not refillable. Additionally, for a distraction, a part of the implant body must be rotated in the bone tissue and/or in the region of the adjacent mucosa which is unfavorable for the healing process and bone formation.

SUMMARY

The technical problem addressed by the present invention is that of providing means and methods for tooth implantation and bone distraction that make it possible to execute implantation methods and bone regeneration methods which overcome the disadvantages from the prior art.

The technical problem addressed by the present invention is that of providing means and methods that make it possible to execute a simplified tooth implantation, when the jawbone must be built up for said purpose.

The technical problem addressed by the present invention is also that of providing distraction devices which have a simple and secure structure.

The technical problem addressed by the present invention can also be considered to be that of providing means and methods with which a bone is built up by means of distraction osteogenesis, required due to a tooth implant placement, such that the individual distraction steps do not have to be executed by a dentist in an office but independently by the patient or an untrained aide.

The technical problem addressed by the present invention is solved by the present invention particularly by providing implants, methods, and uses according to the patent claims.

The technical problem addressed by the present invention is solved by the present invention particularly by providing an implant, comprising an implant body and a distraction membrane, wherein the distraction membrane is connected to the implant body by means of a connection element, wherein the connection element is arranged movably at least over a portion of the longitudinal axis of the implant body, and wherein the movable arrangement of the connection element makes it possible to slide the distraction membrane along the longitudinal axis of the implant body or at least a portion of the longitudinal axis.

In a preferred embodiment, the implant is a temporary implant. In a preferred embodiment, the implant is a thread cutter.

In a preferred embodiment, the implant is a tooth implant. All embodiments of the implant according to the invention described herein thus relate particularly also to a tooth implant according to the invention.

The technical problem addressed by the present invention is therefore preferably solved by providing a tooth implant, comprising an implant body and a distraction membrane, wherein the distraction membrane is connected to the implant body by means of a connection element, wherein the connection element is arranged movably at least over a portion of the longitudinal axis of the implant body, and wherein the movable arrangement of the connection element makes it possible to slide the distraction membrane along the longitudinal axis of the implant body or at least a portion of the longitudinal axis.

The connection element is thus arranged such that it is movable by itself, and thus also the membrane which is connected to the connection element, along at least a portion of the longitudinal axis of the implant body.

In a preferred embodiment, the tooth implant is a temporary implant. In a preferred embodiment, the tooth implant is a thread cutter.

An implant with a structure according to the invention makes it advantageously possible that no additional, particularly elaborate operations are necessary for the bone build-up by distraction osteogenesis than are necessary for the actual placement of the implant itself. The method steps for placing a conventional tooth implant imperatively comprise two surgical steps a) preparing a drill hole, which has a thread, by means of a thread cutter or a temporary implant and subsequently b) placing and engrafting of the final implant.

Prior to said steps, the optional steps "pilot bore in the bone" and "widening of the pilot bore" can be executed. After integration of the final implant, a crown is usually placed onto the final implant. However, this can also be the case with temporary implants. If an implant according to the invention is used in step a), no further, particularly elaborate surgical steps are necessary, even though a bone distraction can be performed between steps a) and b) for the build-up of the bone surrounding the implant. Furthermore, the implant body of an implant according to the invention can be placed advantageously in a conventional manner, and so the dentist does not have to learn a new technique. After placement of the implant body, the membrane can be inserted without any great effort and connected to the implant body by means of the connection element. Due to the continuous or particularly gradual movement of the connection element along the implant body away from the bone with typical distraction speed, the membrane is slowly pulled away from the jawbone, and so a distraction osteogenesis takes place over a desired period of time between the actual steps a) and b). The connection element can be gradually shifted by the patient or an untrained aide as is, for example, common practice for adjusting braces because the connection element is located outside of the mucosa and thus easy to reach. After the bone build-up is completed to the desired extent, the connection element can be removed from the implant body by the dentist without surgical effort. If the membrane of the implant according to the invention is resorbable, the removal of the membrane also requires no further surgical step because said membrane can remain and is degraded between mucosa and bone. If a non-resorbable membrane is used, only a small surgical step is required to remove the membrane. In a typical manner, step b) can then be executed, i.e. removal of the implant body and placement of the final implant. Alternatively, the implant according to the invention can also be a permanent implant, and the implant body can remain in the bone and, for example with a tooth implant, be provided with a permanent crown.

The present invention thus provides an implant that makes it possible to perform the conventional steps a) and b) in a typical manner and, in between, perform a bone distraction for bone build-up without great effort, wherein the individual distraction steps do not necessarily have to be performed by a dentist in an office.

The present teaching thus includes particularly tooth implants and methods for bone regeneration, wherein bones in the jaw region and/or in the periodontal region are to be regenerated.

Furthermore, the implant according to the invention is advantageous because the implant body does not have to be rotated for distraction but remains rigid in the bone, and so the engrafting in the bone is improved and irritation of the mucosa due to rotating the implant is prevented.

An implant according to the invention thus comprises the three components implant body, connection element, and membrane.

In connection with the present invention, a "membrane" refers to a medical membrane which is used for medical procedures for regenerating a bone or with the introduction of bone replacement material in a bone defect. The term bone regeneration refers to both bone regeneration by natural or artificial distraction and the introduction and engrafting of bone replacement material in a bone defect.

In connection with the present invention, a membrane refers to a body which is planar in its flat state, i.e. planar or level. The membrane has a contact surface which is used for apposition or adherence of osteoblasts in the region of a bone defect, and a counterface located opposite of the contact surface. These two surfaces can have any form, for example circular, oval, square, or multisided. Preferably, the contact surface and the counterface are rectangular or circular in their flat state. In the flat state, the size of those two surfaces results from the length and width of the membrane. Furthermore, the membrane has at least one side surface, particularly four side surfaces if it is a rectangular membrane. In the flat state, the size of two of the side surfaces results from the height and the length of a rectangular membrane, and the size of the other two side surfaces results from the height and width of the membrane. According to the invention, the membrane is as thin as possible, i.e. the size of the side surfaces is many times smaller than the size of the contact surface, and in case of a square membrane, the height of the membrane is many times smaller than the length and the width of the membrane.

Preferably, a membrane used according to the invention is used for bone regeneration in the mouth and jaw region, i.e. particularly for bone regeneration on a jaw. The jaw can either be an upper jaw or a lower jaw.

In a preferred embodiment, the membrane is a distraction membrane.

In connection with the present invention, a "distraction membrane" is a medical membrane that can serve or serves as artificial interface in case of a bone distraction. Such a membrane is preferably rigid and break resistant, particularly dimensionally stable. A distraction membrane is preferably designed such that it can be attached to a distraction device and continuously or with single steps removed from the bone, for example, pulled or pushed away from the bone, in a controlled manner at a desired speed by means of the distraction device. A distraction membrane is thus a specific subgroup of medical membranes which, for a person skilled in the art, is readily distinguishable from other medical membranes, which, for example, are used for a simple covering of a bone defect.

In connection with the present invention, a "bone distraction" or a "callus distraction" is a medical procedure for bone regeneration, during which an element is slowly removed from a bone defect, and so an artificial biomechanical pulse, particularly a tension pulse, is exerted on the cells, particularly osteoblasts, located in a callus which generates between the bone defect and the element. The element can be, for example, a bone, a bone fragment, or an artificial body. In particular, the element can be a distraction membrane.

In connection with the present invention, a "biomechanical pulse" is a mechanical force transmission, particularly the transmission of a tensile force, to a cell, particularly osteoblasts, and the biological processes thus triggered in the cell.

In a preferred embodiment, the membrane is made of a resorbable material. As a result, a removal of the membrane after completed bone build-up can advantageously be foregone. Instead, the membrane can remain between mucosa and bone, where it is degraded and decomposed to harmless materials.

In a preferred embodiment, the membrane according to the invention is resorbable, particularly bioresorbable. In a preferred embodiment, the membrane is a bioresorbable distraction membrane.

A person skilled in the art knows different materials for resorbable, i.e. biodegradable membranes and different resorbable membranes from the prior art. Suitable resorbable materials are, for example polylactide or polycaprolactone.

Resorbable distraction membranes from the prior art can also be used for the implant according to the invention. However, an at least two-layered resorbable membrane as described in the following is preferably used.

A particularly preferred membrane, particularly a distraction membrane, for bone formation, preferably as artificial bone fragment for bone formation, has at least two layers and one contact surface and a counterface, wherein the counterface is formed by the first layer, wherein the first layer is made of collagen or predominantly contains collagen, and wherein the second layer is rigid.

An also particularly preferred membrane is a membrane for bone formation with a contact surface and a counterface, wherein the membrane has at least two layers, wherein the counterface is formed by the first layer, wherein the first layer is made of collagen or predominantly contains collagen, and wherein the second layer is made of a bioresorbable plastic or predominantly contains a bioresorbable plastic.

In an embodiment, the membrane can be two-layered. In such case, the contact surface is formed by the second layer. In a preferred embodiment, the membrane is at least triple-layered.

In a preferred embodiment, the membrane is triple-layered. In a preferred embodiment, the membrane is triple-layered, wherein the contact surface is formed by a third layer.

In a preferred embodiment, the membrane is at least triple-layered, wherein the contact surface is formed by a third layer, wherein the third layer is made of a mineral material or predominantly contains a mineral material. In a preferred embodiment, the membrane is triple-layered, wherein the contact surface is formed by a third layer, wherein the third layer is made of a mineral material or predominantly contains a mineral material. The membrane can thus be two-layered or triple-layered. The membrane can also have further layers, for example a fourth layer, a fifth layer, or further layers.

The layer which forms the contact surface, i.e. particularly the second layer or the third layer, is preferably designed such that the contact surface allows for a particularly good adherence of cells, particularly osteoblasts. This is advantageous particularly for a distraction membrane because it is thus ensured that adhering cells of the callus are distracted particularly well by the movement of the membrane, i.e. receive biomechanical pulses.

Surprisingly, it became apparent that with a multilayered structure of a membrane, particularly a distraction membrane, said membrane can be structured such that both the contact surface and the counterface can interact particularly well with the corresponding tissues which bear against the surfaces. The membrane according to the invention is thus of surprisingly good use for autogenic or allogenic bone blocks. The collagen of the first layer of a membrane according to the invention acts on the connective tissue bearing against the counterface. This collagen layer can simultaneously serve as protection for the rigid second layer. The second layer, which preferably is made of a bioresorbable plastic or predominantly contains bioresorbable plastic, serves as framework structure, and so the membrane can be designed so as to be rigid and not bendable, thus being suitable for the use as distraction membrane. Due to the preferred use of the resorbable plastics, a sufficient stability of the membrane is achieved, and so the use of metals, for example titanium, can be foregone. As a result, the entire membrane according to the invention is advantageously resorbable in the body despite sufficient stability, and so the membrane or membrane parts do not have to remain in the body or be surgically removed again. Furthermore, the bioresorbable plastic is well suited as contact surface for cells, particularly osteoblasts of a callus, or can be easily coated with a third layer. In a preferred embodiment, this contact surface can thus also be formed particularly by a third layer which is preferably made of a mineral material or predominantly contains a mineral material. As a result, this layer advantageously corresponds to a natural bone layer of an autogenic or allogenic bone.

The use of a bioresorbable plastic as a framework layer is further advantageous because said framework structure can have a specific design, for example, it can be curved and/or have a predetermined porosity which promotes blood flow and vascularization. The preferred use of a biodegradable plastic as framework layer is further advantageous because this material can be easily cut or otherwise divided, and so the membrane can be cut into the desired form without great effort.

Due to the selected materials, the artificial bone fragment according to the invention can, advantageously, be designed as a membrane despite it having multiple layers, i.e. it can be very thin. Compared to the natural or artificial bone fragment blocks known from the prior art, which have to have a specific thickness, this is advantageous because the thin first layer and the thin second layer and also an optional thin third layer promote improved blood flow and vascularization.

Without wanting to be bound to the theory, the prior art proceeds on the assumption that a shielding of the bone defect from engrafting connective tissue is an important factor for bone regeneration. During the treatment of bone defects, shielding membranes are therefore frequently used which shield the bone defect against the connective tissue and attempt to prevent an engrafting of the connective tissue in the callus forming in the bone defect. As a result, said shielding is frequently considered to be more important than the presence of biomechanical pulses which stimulate the osteoblasts to form bone. Surprisingly, however, providing biomechanical pulses for bone formation appears to be much more important than the shielding of the bone defect from the engrafting of the surrounding connective tissue. Therefore, the membrane according to the invention can preferably be perforated. It can also have pores which extend from the counterface through the membrane to the contact surface. By means of these pores, the bone defect and the callus located at said bone defect as well as the connective tissue, which is separated from the bone defect by the membrane, can be well supplied with nutrients and blood and thus vascularize particularly well. Since the membrane is thin in comparison to bone blocks, the pores are correspondingly short, and so a particularly good connection can be established from the tissue bearing against the counterface to the callus bearing against the contact surface. The fact that connective tissue can also grow into the bone defect region plays a surprisingly minor part as long as the osteoblasts in the callus receive a sufficient amount of biochemical pulses in order to be stimulated to form bone.

The use of a membrane preferably according to the invention results particularly also in a good vascularization of the newly forming bone tissue, particularly if the membrane has pores, preferably according to the invention, which interconnectingly extend through the membrane from the counterface to the contact surface.

In a preferred embodiment, the second layer of the membrane is made of a bioresorbable plastic or predominantly contains a bioresorbable plastic, wherein the second layer has pores with a diameter of at least 10 μm, wherein the pores interconnectingly extend through the second layer from the interface between the second layer and the first layer to the contact surface.

The counterface of a membrane according to the invention is preferably formed by a first layer which is made of collagen or predominantly contains collagen. In a preferred embodiment, the first layer contains at least 50% w/w collagen. More preferably, the first layer contains at least 75% w/w collagen. Particularly preferably, the first layer contains at least 90% w/w, and even more preferably at least 95% w/w collagen. In particular, the first layer can be made entirely of collagen. The collagen can be native collagen or denatured collagen. The collagen can be a collagen selected from the group consisting of one of the collagen types I to XXVIII and mixtures thereof. Preferably, the collagen is a collagen of type I because it is a fibrillary collagen, which can be found in many connective tissues.

Preferably, a "first layer" refers to the layer which forms the counterface and which is made of collagen or predominantly contains collagen.

Preferably, the first layer which is made of collagen or predominantly contains collagen has a layer thickness of at least 0.1 mm and no more than 10.0 mm. Preferably, the layer thickness of the first layer is at least 01. mm. Particularly preferably, the layer thickness of the first layer is at least 0.2 mm. Preferably, the layer thickness of the first layer is at least 0.5 mm. Preferably, the layer thickness of the first layer is at least 1.0 mm. Preferably, the layer thickness of the first layer is at least 2.0 mm. Preferably, the layer thickness of the first layer is no greater than 10.0 mm. Preferably, the layer thickness of the first layer is no greater than 5 mm. Preferably, the layer thickness of the first layer is no greater than 3 mm. Preferably, the layer thickness of the first layer is no greater than 2.5 mm. Preferably, the layer thickness of the first layer is at least 0.5 mm and no greater than 2.5 mm.

Preferably, a "second layer" is the layer of the membrane according to the invention which forms the basic framework of the membrane according to the invention. Preferably, the first layer and the second layer form an interface, i.e. they bear against one another. Preferably, the second layer is rigid. The second layer can be planar or framework-shaped.

Preferred according to the invention, the second layer is made of at least one bioresorbable plastic or predominantly contains at least one bioresorbable plastic. Preferred according to the invention, the second layer is made of a bioresorbable plastic or predominantly contains a bioresorbable plastic. In a preferred embodiment, the second layer contains at least 75% w/w of a bioresorbable plastic. More preferably, the second layer contains at least 95% w/w of a bioresorbable plastic. In a preferred embodiment, the second layer is made of a bioresorbable plastic.

In connection with the present invention, "resorbable plastic" or "bioresorbable plastic" refers to a plastic that is biologically degraded and decomposed in the human body, for example of a patient. The second layer can is made of one single bioresorbable plastic or also two or more different bioresorbable plastics. Preferably, the second layer of a membrane according to the invention is made of a single bioresorbable plastic. A person skilled in the art knows different bioresorbable plastics. A person skilled in the art can readily select bioresorbable plastics, from which membrane layers can be produced which are suitable as stable and particularly rigid framework. Suitable bioresorbable plastics, for example, are polylactic acids, such as polylactide (PLA) and polycaprolactone (PCL).

In a preferred embodiment, the bioresorbable plastic is a polycaprolactone. In a preferred embodiment, the bioresorbable plastic is a polylactide.

In a preferred embodiment, the second layer is designed as a rigid framework and porous. In a preferred embodiment, the second layer is porous.

In a preferred embodiment, the second layer has a layer thickness from at least 0.01 mm to no more than 4 cm. In a preferred embodiment, the second layer has a layer thickness from at least 0.1 mm to no more than 1 cm. In a preferred embodiment, the second layer has a layer thickness from at least 0.1 mm to no more than 3.0 mm. Preferably, the second layer has a layer thickness of at least 0.01 mm. Preferably, the second layer has a layer thickness of at least 0.05 mm. Preferably, the second layer has a layer thickness of at least 0.1 mm. Preferably, the second layer has a layer thickness of at least 0.2 mm. Preferably, the second layer has a layer thickness of at least 0.5 mm. Preferably, the second layer has a layer thickness of at least 1 mm. Preferably, the second layer has a layer thickness of no more than 4 cm. Preferably, the second layer has a layer thickness of no more than 2.5 cm. Preferably, the second layer has a layer thickness of no more than 1 cm. Preferably, the second layer has a layer thickness of no more than 0.5 cm. Preferably, the second layer has a layer thickness of no more than 3 mm. Preferably, the second layer has a layer thickness of no more than 2.5 mm. Preferably, the second layer has a layer thickness of no more than 2 mm.

Preferably, the second layer is rigid, and so, as framework, allows for to use of the membrane as distraction membrane or the transmission of biomechanical pulses.

In connection with the present invention, "rigid" is understood to mean that the layer or the membrane is so break resistant, preferably also dimensionally stable, that it does not bend under the typically occurring forces, i.e. forces that occur with a use according to the invention. In particular, "rigid" means that the membrane does not break, preferably also does not bend, from tensile and compression forces of a magnitude that occur during a callus distraction, i.e. it has sufficient tensile strength.

In a preferred embodiment, the membrane is porous. In a preferred embodiment, the membrane has pores, particularly interconnecting pores.

In a preferred embodiment, the second layer is porous.

In a preferred embodiment, the membrane has at least one perforation. In a preferred embodiment, the membrane is perforated. In a preferred embodiment, the membrane has a plurality of holes, particularly pores, which extend through all layers; in other words, interconnecting pores. Advantageously, such holes allow for the penetration of blood at the contact surface and/or the counterface of the membrane, wherein the blood can then be guided by capillary forces through the membrane to the corresponding other surface, and so a good perfusion of the callus tissues and/or the connective tissue bearing against the membrane is achieved. Furthermore, it is possible for vessels to form in the pores and thus through the membrane, i.e. the growing bone can be well vascularized. The pores preferred according to the invention, particularly interconnecting pores, for example with a diameter of approximately 1 mm, thus allow for the growth of capillaries through the membrane, thus ensuring a very good blood circulation and immune defense in the region of the newly formed bone. The perforations allow for good perfusion of the mucosa which covers the membrane and the regenerate between the membrane and the bone. In a preferred embodiment, the second layer has pores, particularly interconnecting pores.

The interconnecting pores must have a minimum size, i.e. a minimum diameter that allows for erythrocytes with a typical diameter of approximately 7.5 μm to pass through the pores, thus have the diameter of very fine blood vessels. In a preferred embodiment, the pores have a size, i.e. a diameter, of at least 0.005 mm and no more than 1.5 mm. In a preferred embodiment, the pores have a size of at least 0.01 mm and no more than 1.5 mm. In a preferred embodiment, the pores have a size of at least 0.005 mm. In a preferred embodiment, the pores have a size of at least 0.01 mm. Preferably, the pores have a diameter of at least 0.1 mm. Preferably, the pores have a diameter of at least 0.3 mm. Preferably, the pores have a diameter of at least 0.5 mm. Preferably, the pores have a diameter of approximately 1 mm. Preferably, the pores have a diameter of no more than 1.5 mm. Preferably, the pores have a diameter of no more than 1.3 mm. Preferably, the pores have a diameter of no more than 1.2 mm.

Preferably, the pores extend through the membrane. Preferably, the pores extend from the counterface through the membrane to the contact surface. The pores are thus preferably interconnecting, thus extending from the counterface to the contact surface.

The number of pores preferably depends on the size of the membrane. For example, a membrane with a length of approximately 20 mm and a width of approximately 10 mm can have approximately ten to twenty pores. Such a ratio of number of pores to membrane surface results in an optimum between the total pore surface, which promotes blood circulation, and the adherence surface for osteoblasts which adhere to the membrane during the distraction process.

In a preferred multilayered, the contact surface can be formed by the second layer or a further, for example, third layer. The contact surface is preferably designed such that it allows for an adherence of cells, particularly osteoblasts. Preferably, the contact surface is rough. Preferably, the contact surface is porous. In addition to the preferred interconnecting pores, the contact surface can have further pores which are not interconnecting and only protrude into the membrane, and so cells, particularly osteoblasts can adhere particularly well.

A particularly good contact surface can be formed by a further, particularly third, layer, preferably by a layer made of a mineral material.

Preferably, the contact surface of the membrane according to the invention is formed by the second layer of by a third layer. Preferably, the contact surface is formed by a third layer which is made of a mineral material or predominantly contains a mineral material. A person skilled in the art knows differently suitable mineral materials. The mineral material of the third layer is preferably hydroxylapatite and/or tricalcium phosphate. Preferably, the third layer is formed from hydroxylapatite or contains hydroxylapatite, particularly contains predominantly hydroxylapatite. In an alternative embodiment, the third layer is formed from tricalcium phosphate or contains tricalcium phosphate, particularly contains predominantly tricalcium phosphate. Alternatively, the mineral material of the third layer can contain hydroxylapatite and tricalcium phosphate. Preferably, the third layer is porous. Preferably, the interconnecting pores extend through the third layer. Preferably, the membrane according to the invention has thus a porous mineral third layer which forms the contact surface of the membrane. In a preferred embodiment, the third layer has a layer thickness from at least 1.0 μm to no more than 1 mm. Preferably, the third layer has a layer thickness of at least 1.0 μm. Preferably, the third layer has a layer thickness of at least 2.0 μm. Preferably, the third layer has a layer thickness of at least 5.0 μm. Preferably, the third layer has a layer thickness of at least 10 μm. Preferably, the third layer has a layer thickness of no more than 1 mm. Preferably, the third layer has a layer thickness of no more than 0.5 mm. Preferably, the third layer has a layer thickness of no more than 0.2 mm.

Preferably, the membrane has a thickness of at least 0.1 mm.

The preferred membrane thicknesses result particularly from adding the preferred thicknesses of the individual layers. Preferably, the membrane has a thickness from at least 0.2 mm to no more than 13 mm. Preferably, the membrane has a thickness of at least 0.2 mm. Preferably, the membrane has a thickness of at least 0.5 mm. Preferably, the membrane has a thickness of no more than 13 mm. Preferably, the membrane has a thickness of no more than 10 mm. Preferably, the membrane has a thickness of no more than 5 mm. Preferably, the membrane has a thickness of no more than 3 mm.

In a preferred embodiment, the membrane has a hole for attaching the connection element. In a preferred embodiment, the membrane has a hole which is located particularly preferably in the middle surface region of the membrane and through which a connection element can be inserted, or into which a connection element can be screwed, inserted, glued, or clicked. In a preferred embodiment, the hole has a thread. The thread can be formed particularly by the perforated wall located in the second layer. Therefore, the membrane preferably has a hole, wherein the hole extends through the second layer, particularly through the bioresorbable plastic of the second layer, and the hole has a thread in the region of the second layer. Advantageously, the connection element can be screwed into said thread.

In an alternative embodiment, the hole has no thread, for example, when a connection element is inserted, glued, clicked into the hole.

In a preferred embodiment, the connection element is located on the counterface of the membrane or, as seen looking from the counterface, extends into the membrane. In a preferred embodiment, the edges of the membrane are rounded.

The membrane can be designed so as to be flat or curved. Particularly in case of membranes with smaller dimensions, the membrane can preferably be flat, i.e. level.

However, particularly for the use in the jaw region, the membrane can alternatively also be curved. In a preferred embodiment, the membrane is curved. In a preferred embodiment, the membrane, particularly if it is a membrane for use in the jaw region, is curved in a U-shaped manner. A membrane curved in a U-shaped manner can completely cover a bone defect, particularly in the jaw region, i.e. cover said region from above and from both sides. Having a cross-section similar to the letter "U," it encompasses the jaw bone vestibularly and lingually. The surface is thus also extended to the side walls of the jaw, where, as a result, artificial pulses are also released. This can then serve as ridge extension since the clinical problem of a ridge extension in conjunction with ridge heightening very often arises in combination.

In a preferred embodiment, at least a portion of the contact surface and the counterface is curved. Therefore, the membrane is preferably curved over at least a portion of the length or width of the membrane.

In a preferred embodiment, the edges between the contact surface and the at least one side surface and/or the counterface and the at least one side surface are rounded.

In an alternative embodiment of the invention, the edges formed by two side surfaces each can be rounded.

In a preferred embodiment, the membrane has rounded edges.

In an alternative embodiment, the membrane according to the invention is a membrane for periodontal regeneration by means of distraction. Periodontal regeneration refers to a regeneration of the periodontium, i.e. not only a regeneration of the bone but also of the periodontal ligament, the periodontal membrane, the gingiva, and the papillae, for example by "Guided Tissue Regeneration" (GTR). In a preferred embodiment, the membrane for periodontal regeneration is dimensioned so small that it can also be used in interdental spaces. In a preferred embodiment, the membrane for periodontal regeneration is very thin. In a preferred embodiment, the membrane for periodontal regeneration is shaped such that it has at least one flap or one segment which can be inserted in an interdental space.

Alternatively, the membrane can also be non-resorbable, i.e. be made of non-resorbable materials or contain same. A person skilled in the art knows different non-resorbable membranes, particularly distraction membranes, from the prior art. These can also be used with an implant according to the invention.

In a preferred embodiment, the membrane is made of a biogenic material.

A preferred embodiment contains a non-resorbable membrane. In a preferred embodiment, the membrane is made of titanium.

The membrane can also be made of ceramic, polymers, composites, or collagen, or contain these materials.

In a preferred embodiment, the membrane is sandblasted. In a preferred embodiment, the contact surface of the membrane is sandblasted.

In a preferred embodiment, the contact surface of the membrane is coated.

A person skilled in the art will readily be able to determine a suitable size for the membrane. The minimum size of a preferred membrane with a hole for guiding the implant body through it results from the diameter of the implant body and the diameter of the hole resulting therefrom. Preferably, the membrane has a diameter of at least 3 mm, more preferably at least 4 mm, particularly preferably at least 5 mm, for example approximately 6 to 8 mm, particularly 7.15 mm. The diameter specification relates to circular membranes. In case of angular membranes, particularly rectangular membranes, the aforementioned minimum diameter values relate to the minimum length and minimum width of the membrane.

The size of the membrane can be adjusted to the size of the bone surface on which a bone is supposed to be built up.

Since the membranes are dimensionally stable, bigger membranes in the cm range can be used, for example membranes with a diameter or a length and width of approximately 1 cm, approximately 2 cm, approximately 5 cm, or bigger.

In a preferred embodiment, the membrane is multilayered, particularly triple-layered. In an alternative embodiment, the first layer of the membrane which forms the counterface is made of collagen, for example with a layer thickness from 1 mm to 3 mm, particularly of approximately 2 mm. Preferably, the middle layer is made of a metal, particularly titanium. Preferably, the third layer which forms the contact surface is made of hydroxylapatite. Therefore, a triple-layered membrane with a collagen layer, a titanium layer, and a hydroxylapatite layer is preferred.

In an embodiment, the membrane is curved such that it has the shape of a part of a spherical shell, for example a hemispherical shell. In a further embodiment, the membrane is curved such that it has the shape of a cylindrical shell.

In a preferred embodiment, the curvature has a radius that corresponds to the radius of a bone to be treated, for example a long bone or a cranial bone.

In a preferred embodiment, the curvature has a radius which corresponds to the radius of a jaw bone ridge.

In a preferred embodiment, the curvature has a radius of at least 5 mm. In a preferred embodiment, the curvature has a radius of no more than 15 mm. In a preferred embodiment, the curvature has a radius of at least 5 mm and no more than 15 mm.

The membrane according to the invention can be intended for multiple or single use. Preferably, the membrane is intended for a single use since this is common practice with medical membranes and the adhesion of the surface of the membrane diminishes due to contact with body fluid. The membrane according to the invention can be intended for single use particularly if it was produced individually for a specific bone defect and/or if it has biodegradable components which decompose during the use of the membrane.

With regard to form and size, the membranes can be ready-made or individually adjusted to the bone defect to be treated.

In a preferred embodiment, the distraction membrane has a hole, through which the implant body extends.

In a preferred embodiment, the connection element comprises a transmission, particularly a self-locking transmission, for moving the membrane along the longitudinal axis of the implant body.

The connection element is used to attach the membrane to the implant body and to slide the membrane along the implant body in a controlled manner.

In a preferred embodiment, the connection element is attached on the counterface of the membrane or inserted in or preferably screwed into a hole of the membrane.

Preferably, the connection element connects the membrane and the implant body such that the contact surface of the membrane is oriented in the direction of the tip of the implant body, and that the connection element is oriented in the direction of the head of the implant body.

A person skilled in the art readily knows different designs of a suitable connection element which allow for the connection of the membrane with the implant body according to the invention and which allow for a moving, particularly controlled moving of the membrane along the implant body.

Preferably, the connection element has a point of application for a tool, and so the connection element can be moved or shifted in a controlled manner along the implant body by means of the tool. Preferably, the point of application for the tool is on the actuating body of the connection element.

In a preferred embodiment, the hole in the distraction membrane has an internal thread and the connection element has an external thread, wherein the external thread of the connection element can be screwed into the internal thread of the distraction membrane.

In an alternative embodiment, it is possible that the hole of the membrane has no thread prior to screwing the connection element into said hole, but instead said thread is milled by the external thread of the connection element when said connection element is screwed into the hole.

In an alternative embodiment, it is possible that the hole of the membrane has no thread and the connection element is, for example inserted, engaged, glued, or clicked into the hole of the membrane.

In a preferred embodiment, the connection element is connected to the membrane by means of a tongue and groove connection or by means of an adhesive connection, an insertion connection, or a snap-lock connection, or a click connection.

In a preferred embodiment, the connection element has a spacer sleeve.

In a preferred embodiment, the connection element is designed as a spacer sleeve.

Preferably, the spacer sleeve has, at least to some extent, a conical form.

In an alternative embodiment, the connection element has a spacer sleeve and at least one further partial element. Preferably, the at least one further partial element acts as movable connection of the connection element with the implant body.

In the prior art, a spacer sleeve is a metallic body which is used for implants. A spacer sleeve is supposed to bridge the distance between bone and mucosa. The spacer sleeve is usually inserted during the healing phase of an implant.

Advantageously, a spacer sleeve can be present as component of the connection element in an implant according to the invention. Preferably, the spacer sleeve forms at least that part of the connection element which is directly connected to the membrane. In this embodiment, the spacer sleeve can advantageously fulfil two tasks. The spacer sleeve can allow for a secure and simple connection as intermediate element between the membrane and the partial element of the connection element which is mounted on the implant body. In this design, the spacer sleeve is also located in a position, in which it extends through the oral mucosa, particularly when used in the jaw region, thus forming the boundary between the membrane located below the mucosa and the further partial elements of the connection element. Thus, the membrane and the spacer sleeve can form a smooth surface without sharp edges which comes in contact with the mucosa, and so the mucosa, during distraction, does not rub against the implant body, particularly sharp-edged parts of the implant body, such as the threaded part or the optional toothed rack part.

Preferably, the membrane thus has a hole through which the implant body extends; the implant body also extends through the spacer sleeve, and the spacer sleeve is inserted in or preferably screwed into the hole of the membrane.

In a preferred embodiment, the connection element is designed as spacer sleeve and wherein the membrane is attached to a surface of the spacer sleeve. Preferably, the membrane is glued with the counterface to the surface of the spacer sleeve, for example with fibrin glue.

In an alternative embodiment, the membrane is formed by a surface of the spacer sleeve.

In such case, the spacer sleeve is designed such that it has a surface which is oriented in the direction of the tip of the implant body, and a membrane is either applied to said surface or said surface is designed so as to be membranous, said surface being particularly coated, for example coated with hydroxylapatite.

Preferably, the spacer sleeve has a conical form. The cone of the spacer sleeve increases preferably in the direction of the tip of the implant body. Thus, the surface of the spacer sleeve, onto which either a membrane is applied or which is designed so as to be membranous, is formed by the base surface of the conical cone. Preferably, the size of said base surface corresponds to the size of the membrane surface. Since the size of the base surface of the cone is particularly also determined by the angle between a surface line and the cone axis, the membrane surface size can thus be determined advantageously by a spacer sleeve with corresponding angle, yet the height of the spacer sleeve does not change. As a result, different spacer sleeves with the same height but different base surface can be used with an implant according to the invention and thus in a simple manner different membrane sizes. In an alternative embodiment, the cone of the spacer sleeve can decrease in the direction of the tip of the implant body, or the spacer sleeve has no cone, for example if only a small membrane surface is required.

In a preferred embodiment, such a spacer sleeve is made of a bioresorbable material.

In a preferred embodiment, the membrane is connected to a spacer sleeve by means of a clamping fit, and the cone increases in the direction of the tip of the implant body.

In a possible embodiment, the spacer sleeve is designed such that it is screwed onto the implant body as connection element and can be moved along the implant body through rotation. In this case, the membrane is preferably rotatably attached to the spacer sleeve, and so the spacer sleeve but not the membrane rotates during distraction.

In a further alternative embodiment of an implant with a spacer sleeve according to the invention, the spacer sleeve is connected to the membrane by means of a tongue and groove connection or by means of an adhesive connection, an insertion connection, or a snap-lock connection, or a click connection.

The preferred implant with spacer sleeve according to the invention can furthermore be advantageously designed such that neither the implant body nor the spacer sleeve have to be rotated, and so an irritation of the mucosa caused by rotating the implant body and/or the spacer sleeve is prevented.

For a simple and secure connection of the membrane with the connection element by means of a screw connection between a spacer sleeve and the membrane, two alternative embodiments can preferably be provided.

In the first embodiment, the first end of the spacer sleeve, which is screw-connected with the membrane, has an external thread. The second end of the spacer sleeve, which is screw-connected with the at least one further partial element, has a second thread which is working in opposite direction of the first thread. The second thread can be an internal thread or an external thread. The at least one further partial element of the connection element, which is screw-connected with the spacer sleeve, has a corresponding external thread or internal thread. For connecting the membrane with the connection element, it is sufficient in this embodiment to rotate the spacer sleeve, and so the first thread of the spacer sleeve screws into the hole of the membrane and the second thread of the spacer sleeve simultaneously connects to the corresponding thread of the at least one further partial element of the connection element. Therefore, by means of one single rotation, the spacer sleeve can be connected to the membrane and also to the at least one further part of the connection element.

In the second alternative embodiment, the first thread of the spacer sleeve and the second thread of the spacer sleeve are working in the same direction. The thread connection between the spacer sleeve and the at least one further element of the connection element is designed such that the spacer sleeve can be screwed beyond the end location point into the thread or onto the thread of the at least one further partial element of the connection element. In this embodiment, the spacer sleeve is screwed onto the thread or into the thread of the at least one further partial element of the connection element beyond the end point. Then the first thread of the spacer sleeve is brought into contact with the hole of the membrane. When the spacer sleeve is rotated back to the end point in respect of the at least one further partial element of the connection element, the first thread of the spacer sleeve simultaneously screws into the hole of the membrane, so once the end point is reached, the spacer sleeve is connected to the membrane and also to the at least one further partial element of the connection element.

A person skilled in the art naturally also knows many further structural designs which allow for a connection of the connection element to the membrane by means of a spacer sleeve.

In a preferred embodiment, the connection element has a housing.

In a preferred embodiment, the housing is designed as spacer sleeve.

In an alternative embodiment, the housing of the connection element is connected to the spacer sleeve.

In a preferred embodiment, the connection element has a spacer sleeve and a housing, wherein the housing has an external thread or an internal thread on one end, and wherein the spacer sleeve is, at least to some extent, conical, and wherein the spacer sleeve has, on the first end with the smaller diameter, an external thread for screwing into the hole of the membrane, and wherein the spacer sleeve, on the second end which is opposite the first end, has an internal thread, into which the external thread of the housing can be screwed, or wherein the spacer sleeve, on the second end which is opposite the first end, has an external thread, into which the internal thread of the housing can be screwed.

The spacer sleeve can be screwed into the membrane in a self-cutting manner. Alternatively, the spacer sleeve with an external thread is screwed into a corresponding internal thread in the membrane.

The spacer sleeve can form the lower part of the connection element or, beyond that, also cover, or to some extent cover, the further parts of the connection element.

In a preferred embodiment, the implant body, along its longitudinal axis, has a first lower portion with a thread, and a second portion above the lower portion. Preferably, the connection element can be shifted, or shifted in a controlled manner, along the second portion above the lower portion. Preferably, the second portion is designed as toothed rack.

In a preferred embodiment, the connection element has a housing with a passage and a threaded body, wherein the part designed as toothed rack of the implant body is inserted in longitudinal extension through the passage essentially without play through the housing, and wherein the threaded body is rotatably mounted in the housing such that the threaded body and the toothed rack are in active mesh.

In a preferred embodiment, the implant is based on the system of a connection element with an adjusting nut with internal thread, which is rotatably mounted in the housing and screwed onto the implant body. If this adjusting nut is rotated, it moves together with the housing and thus the connection element with membrane moves along the implant body. Preferred is also an embodiment, in which the connection element is designed as spacer sleeve, wherein the membrane is attached to a surface of the spacer sleeve. Or, as described above, the membrane is formed by a surface of the spacer sleeve.

In an alternative embodiment, the implant is based on the system of a connection element with a worm gear, an implant body with a toothed rack section, and a membrane, wherein the rotatory movement of a threaded body, particularly a screw, is transformed into a translational motion of the connection element and thus the membrane on the toothed rack. Preferably, the threaded body, particularly the screw, has a thread with a pitch p=0.1 to 0.5 mm, particularly approximately 0.3 mm, particularly 0.3 mm, and the toothed rack is toothed accordingly. A pitch of 0.3 mm of the threaded body, for example, results in a stroke of 0.3 mm per full rotation of the threaded body.

A further alternative embodiment is an implant, the implant body of which has a woodscrew thread in the apical third, particularly as a thread cutter, and the rest is provided with a further thread. On the further thread, the spacer sleeve is moved similar to a screw-nut.

In this embodiment, the spacer sleeve rotates, irritating the engrafting tissue, but advantageously, a simpler structure is provided which can consist of only one part.

In a preferred embodiment, the connection element and the spacer sleeve are made of at least one biogenic material. Preferably, the material is not biodegradable.

In a preferred embodiment, the connection element and the spacer sleeve are made of titanium or a titanium alloy, particularly the material TIAl4V, or they are made of zirconium or a stainless steel, or contain same, particularly predominantly contain same.

In an alternative embodiment, the connection element and the spacer sleeve can also be made of a biodegradable material, particularly a biodegradable plastic such as polylactide or polycaprolactone, or contain same, particularly predominantly contain same.

Preferably, the implant body is made of a biogenic and non-biodegradable material.

Preferably, the implant body is made of a metal, particularly titanium or zirconium, particularly if the implant according to the invention is a tooth implant. A person skilled in the art knows suitable materials for a tooth implant body.

Alternatively, the implant body can be made of a biogenic and biodegradable material, for example, if the implant according to the invention is not a tooth implant.

A person skilled in the art knows suitable implant body forms. Particularly, the lower part of the implant body, having a thread for screwing into a bone, can be based on a threaded part of an implant from the prior art.

For example, the implant body can have a woodscrew thread in the apical third, particularly as a thread cutter.

In a preferred embodiment, the implant comprises a crown. In a preferred embodiment, the tooth implant comprises a crown.

The technical problem addressed by the present invention can also be considered to be that of providing means and methods for bone distraction that make it possible to also execute bone regeneration procedures outside the jaw region and which overcome the disadvantages from the prior art.

The technical problem addressed by the present invention can also be that of providing distraction devices which have a simple and secure structure.

An implant according to the invention can advantageously also be used generally for bone build-up by distraction because it can also be used for application outside the jaw or in the jaw without the implant also having to function as tooth replacement. For such a use, the implant is also characterized by a simple structure and favorable handling.

In an alternative embodiment, the implant is not a tooth implant.

In an alternative embodiment, the implant body and particularly preferably the entire implant according to the invention can be resorbable, i.e. be made of resorbable materials. This is particularly advantageous if the implant is not a tooth implant but is merely used for bone build-up by distraction, wherein it can be used not only in the jaw region but also on other bones. In such case, a resorbable implant according to the invention is advantageous because the implant does not have to be surgically removed after completed distraction but instead can remain and be degraded in the body.

In an alternative embodiment, the implant body is made of a resorbable material.

In a preferred embodiment, the entire implant is made of resorbable materials.

In a preferred embodiment, the implant according to the invention is used for a bone distraction.

In a preferred embodiment, the tooth implant according to the invention is used for a bone distraction and simultaneously as temporary implant or permanent implant.

The implant according to the invention can also be designed as permanent implant and particularly permanent tooth implant. In such case, the connection element can be removed after completed bone distraction and replaced with a crown.

The present invention also relates to an implant according to the invention to be used for callus distraction, particularly for building up a bone, particularly jaw bone, by distraction.

In a preferred embodiment, the implant is suitable for callus distraction. In a preferred embodiment, the implant is suitable for bone regeneration.

In a preferred embodiment, the tooth implant is suitable for callus distraction in the jaw region. In a preferred embodiment, the tooth implant is suitable for bone regeneration in the jaw region. In a preferred embodiment, the tooth implant is suitable for periodontal regeneration in the jaw region.

In a preferred embodiment, the implant is provided for use in a medical procedure, particularly in a surgical procedure.

In a preferred embodiment, the implant is provided for use during bone regeneration by distraction, particularly in the jaw region.

In a preferred embodiment, the implant according to the invention is suitable to be used for bone distraction, particularly of a jaw bone. In a preferred embodiment, the implant according to the invention is used for bone distraction, particularly of a jaw bone.

Preferably, the distraction with the implant according to the invention is executed with a distraction speed from at least 0.2 mm per day to no more than 2.5 mm per day, particularly from at least 0.5 mm per day to no more than 2 mm per day. Particularly preferably, the distraction speed is approximately 1 mm per day.

The present invention also relates to an implant according to the invention to be used for callus distraction, particularly for the build-up of a jaw bone by distraction.

The present invention also relates to an implant according to the invention to be used for periodontal regeneration by distraction.

In an alternative embodiment, the implant according to the invention is a tooth implant with a membrane for periodontal regeneration. Periodontal regeneration refers to a regeneration of the periodontium, i.e. not only a regeneration of the bone but also of the periodontal ligament, the periodontal membrane, the gingiva, and the papillae, for example by "Guided Tissue Regeneration" (GTR).

The present invention also relates to a kit, containing an implant according to the invention. The present invention also relates to a kit, containing the implant main part of an implant according to the invention, at least one connection element, and at least one membrane, particularly a plurality of different membranes.

Preferably, the kit contains instructions for use. Preferably, the instructions for use contain information as to how the kit can be used for placing the implant and distracting a callus.

A preferred embodiment is a kit according to the invention for use in medical procedures, particularly surgical procedures, preferably for a bone distraction, particularly in the jaw region. A further preferred embodiment is the use of a kit according to the invention for producing an implant according to the invention.

The present invention also relates to the use of an implant according to the invention in a medical procedure, particularly a surgical procedure.

The present invention also relates to the use of an implant according to the invention for callus distraction, particularly in the jaw region, particularly for building up a jaw bone by distraction.

The present invention also relates to methods for callus distraction, particularly for building up a jaw bone by distraction, wherein a membrane of an implant according to the invention is applied to a bone defect to be regenerated and tensile stress is applied to said membrane by means of the connection element. The membrane is thus removed from the bone defect at a specific speed with the toothed rack. Preferably, the speed is 0.2 mm to 2.5 mm per day, particularly 0.5 mm to 2 mm per day. Particularly preferably, the speed is approximately 1 mm per day. Without being bound to the theory, particularly a distance of approximately 1.5 mm between membrane and bone is advantageous for such distraction methods at the beginning of the method.

The slow removal of the membrane from the bone defect can be continuous or discontinuous, for example daily or every half-day.

The present invention also relates to methods for callus distraction, particularly for building up a jaw bone by distraction, containing the following steps:

a) Implanting the implant according to the invention in a bone, preferably a jaw bone, wherein the implant is a temporary implant;

b) Executing a distraction osteogenesis with the membrane of the implant according to the invention; particularly as described above;

c) Removing the fastening element from the implant body;

d) Removing the temporary implant body from the bone;

Preferably, a distraction in the jaw region is followed by step e) inserting and engrafting of a permanent implant in the bore hole of the removed implant according to the invention.

The present invention also relates to methods for implanting a permanent tooth implant according to the invention, containing the following steps:

a) Implanting the implant according to the invention in a bone, preferably a jaw bone, wherein the implant is a permanent implant;

b) Executing a distraction osteogenesis with the membrane of the implant according to the invention; particularly as described above;

c) Removing the fastening element from the implant body;

Preferably, a crown is placed on a tooth implant with the methods according to the invention.

Preferably, a bioresorbable membrane which does not have to be removed is used for the methods according to the invention. Alternatively, a non-biodegradable membrane, for example a membrane made of titanium, can be used. Said membrane is preferably also removed after the fastening element is removed from the implant body.

Preferably, step a) of the method according to the invention contains the following substeps:

a1) Implanting the implant body in the bone;

a2) Placing of the membrane onto the implant body and applying the membrane to the bone defect;

a3) Placing of the connection element onto the implant body; and a4) Attaching the connection element to the membrane, for example by screwing, inserting, engaging, clicking or gluing of the connection element, particularly the spacer sleeve of the connection element to the hole of the membrane.

Alternatively, the following substeps can also be provided:

a1) Applying the membrane to the bone defect;

a2) Inserting the implant body in the hole of the membrane and implanting the implant body in the bone;

a3) Placing the connection element onto the implant body; and a4) Attaching the connection element to the membrane, for example by screwing, inserting, engaging, clicking or gluing of the connection element, particularly the spacer sleeve of the connection element to the hole of the membrane.

Prior to step a), the optional steps "setting a pilot bore in the bone" and "widening the pilot bore" can be executed. After the healing of the final implant, a crown is usually placed on the final implant. However, this can also be the case with temporary implants.

Advantageously, step b), particularly the gradual shifting of the connection element, can be executed by the patient or an untrained aide, for example with the help of a tool which is applied to a point of application for the tool on the connection element, preferably on the actuating body of the connection element.

Preferred embodiments of the invention are also contained in the dependent claims.

BEST DESCRIPTION OF THE DRAWINGS

In the following, the invention is explained in more detail using the drawings.

DETAILED DESCRIPTION

Naturally, preferred details of the embodiments shown in FIGS. 1 to 7 can also be combined.

Figure 1:
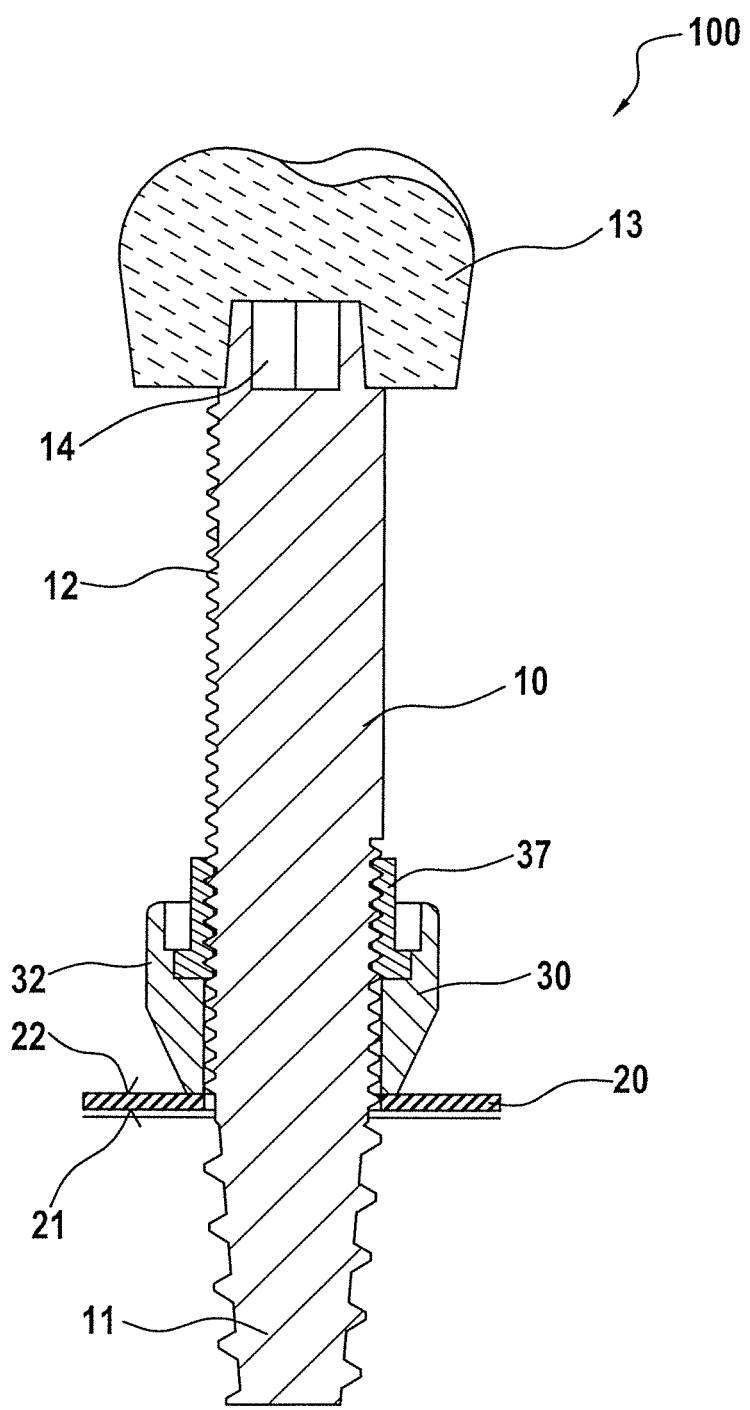
FIG. 1 shows the cross-section of a preferred embodiment of an implant according to the invention.

FIG. 1 shows the cross-section of a preferred embodiment of an implant (100) according to the invention. The implant (100) comprises an implant body (10), a distraction membrane (20), and a connection element (30).

The apical region (11) of the implant body (10) has a thread for screwing or boring the implant body (10) into a bone. The coronal section (12) of the implant body (10) is designed as toothed rack. The implant body (10) has a hole (14), over which a crown (13) can be attached.

The distraction membrane (20) has a contact surface (21) and a counterface (22). The contact surface (21) is preferably formed by a coating, for example, made of a mineral material.

The distraction membrane (20) is connected to the implant body (10) by means of the connection element (30) such that the membrane (20) can be moved or shifted along the implant body (10). The connection element (30) has a to some extent conical spacer sleeve (32). The membrane (20) is engaged, screwed, or glued into said spacer sleeve (32). An adjusting nut (37), having an interior thread, is rotatably mounted in the spacer sleeve (32). By rotating the adjusting nut (37), the spacer sleeve (32) and thus also the membrane (20) can be shifted along the implant body (10). The adjusting nut (37) is thus a rotatably mounted threaded body which is in active mesh with the toothed rack of the coronal section (12) of the implant body (10).

Figure 2A:
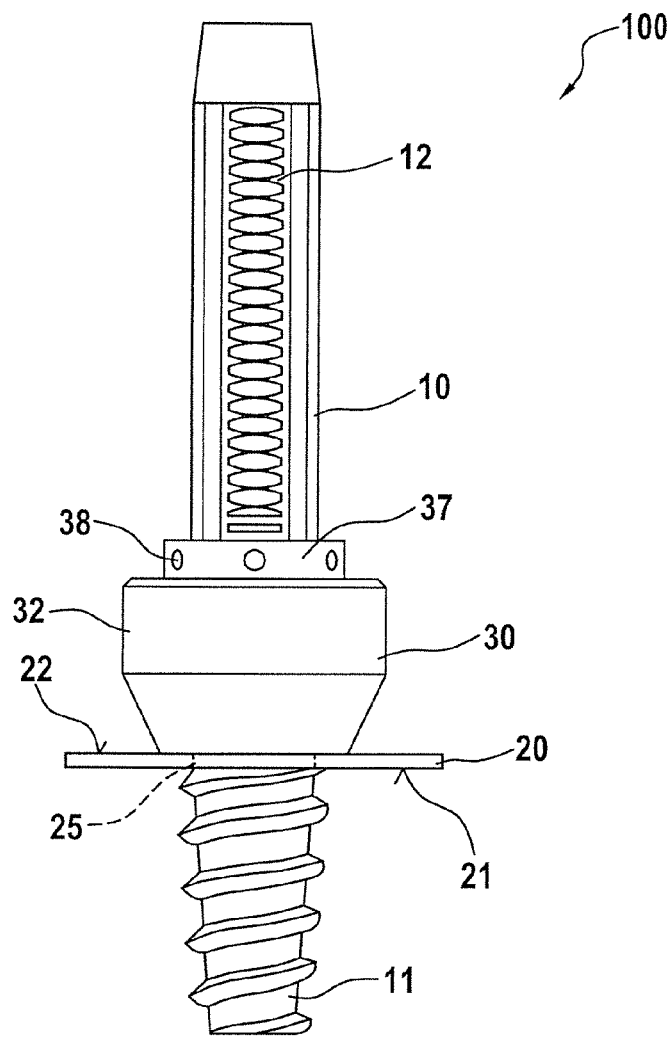
FIG. 2 shows a side view and a top view of the embodiment according to the invention from FIG. 1.
Figure 2B:
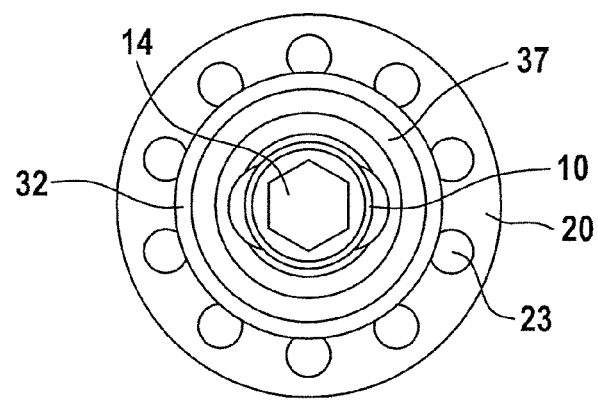

FIG. 2 shows a side view (A) and a top view (B) of the implant (100) according to the invention from FIG. 1.

It again shows the implant body (10) with apical region (11) and coronal section (12) and hole (14) for attaching a crown, the distraction membrane (20) with contact surface (21) and counterface (22), and the connection element (30) with spacer sleeve (32) and adjusting nut (37).

The membrane has interconnecting perforations or pores (23) which allow for a material and blood exchange between the tissue bearing against the contact surface (21) and the tissue bearing against the counterface (22). The implant body (10) is guided through a hole (25) in the membrane (20).

The adjusting nut (37) has a plurality of points of application (38) for a tool, and so the adjusting nut can be rotated in a simple manner and thus be moved with its internal thread along the toothed rack.

Figure 3A:
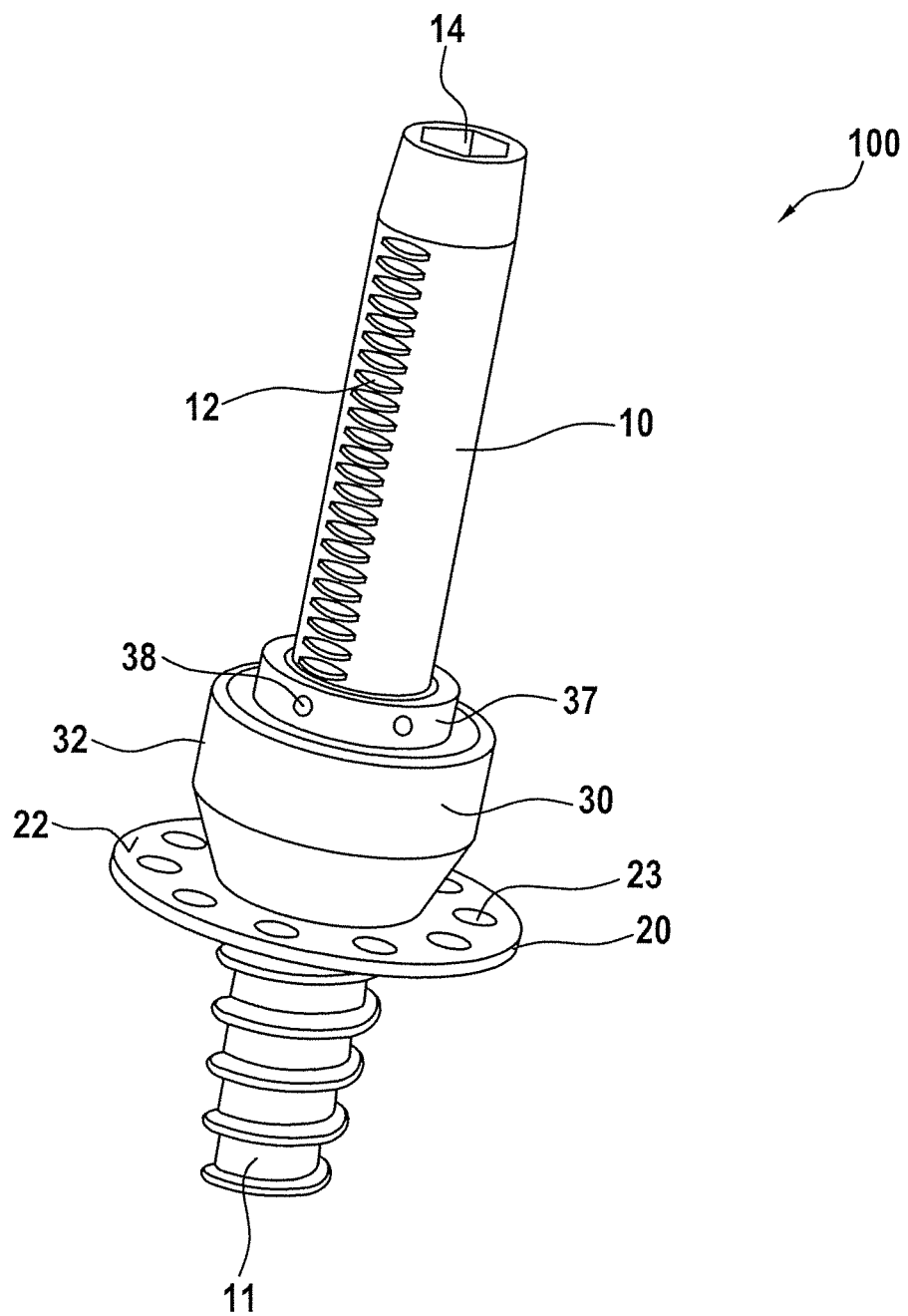
FIG. 3 shows the embodiment from FIG. 1 with connected and not yet connected membrane.

FIG. 3 shows the implant (100) according to the invention from FIG. 1 with connected membrane (A) and not yet connected membrane (B).

It again shows the implant body (10) with apical region (11) and coronal section (12) with toothed rack and hole (14) for attaching a crown, the distraction membrane (20) with contact surface (21), counterface (22), and interconnecting perforations or pores (23), and the connection element (30) with spacer sleeve (32), and adjusting nut (37) with a plurality of points of application (38).

Figure 3B:
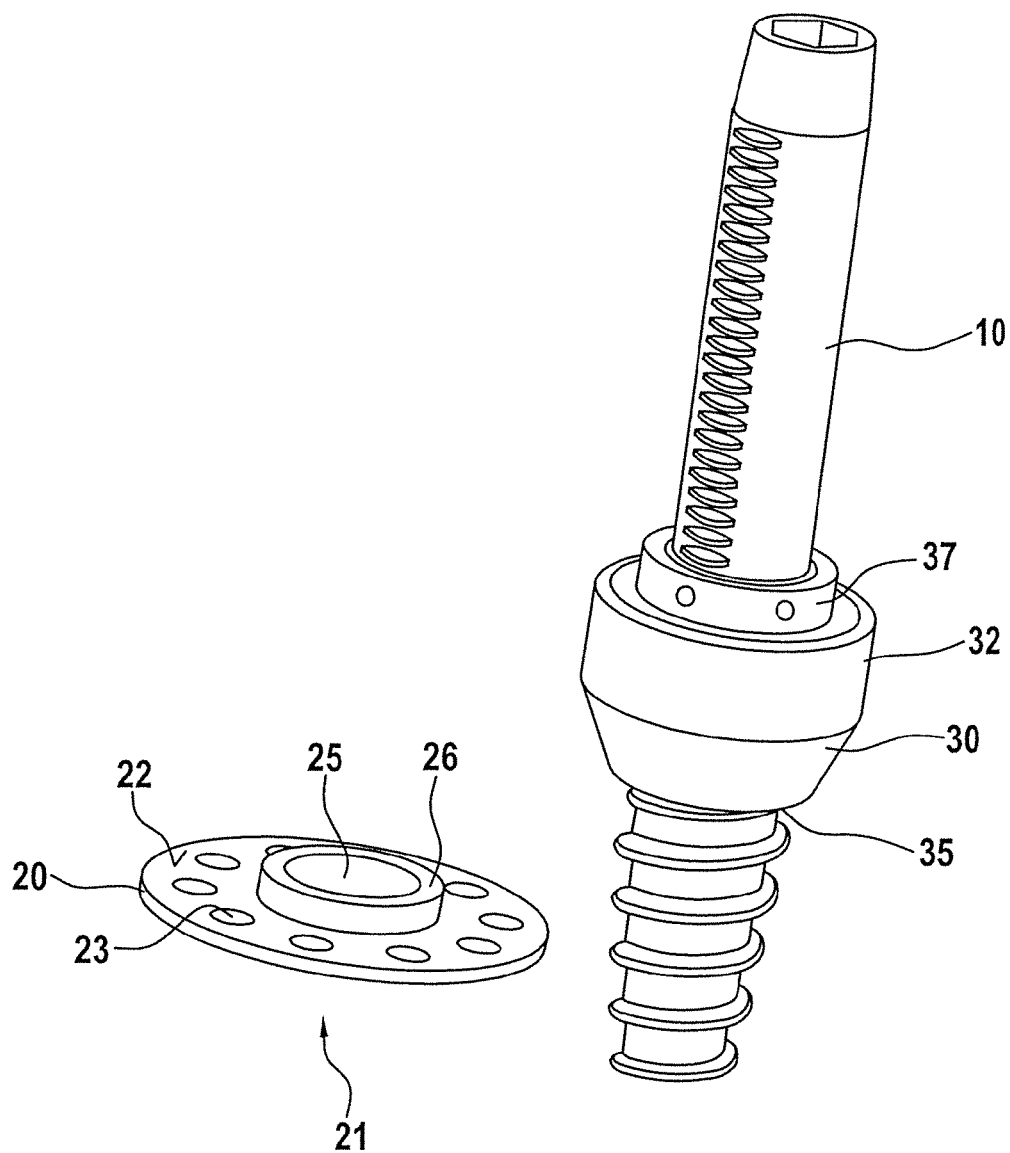

In FIG. 3B, the membrane is not yet connected to the spacer sleeve (32). For attaching the membrane (20), the implant body (10) can be guided through the hole (25) in the membrane (20). Then, the membrane (20) with the ring (26), which for example can be designed as a groove of a tongue and groove connection or as a snap-in element, can be clicked in or engaged in the spacer sleeve (32), wherein the implant body (10) is already guided through a hole (35) in the spacer sleeve (32).

Figure 4A:
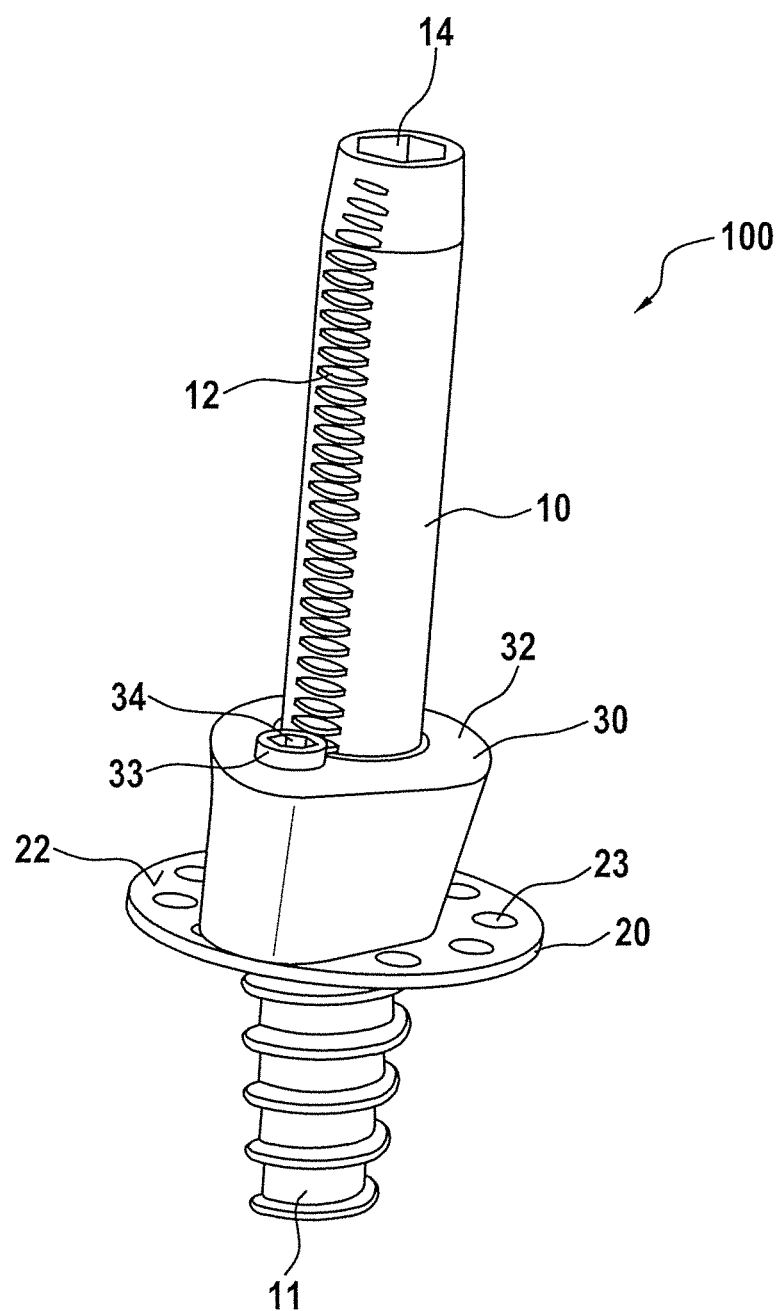
FIG. 4 shows a side view and cross-section of an alternative embodiment of the implant according to the invention.
Figure 4B:
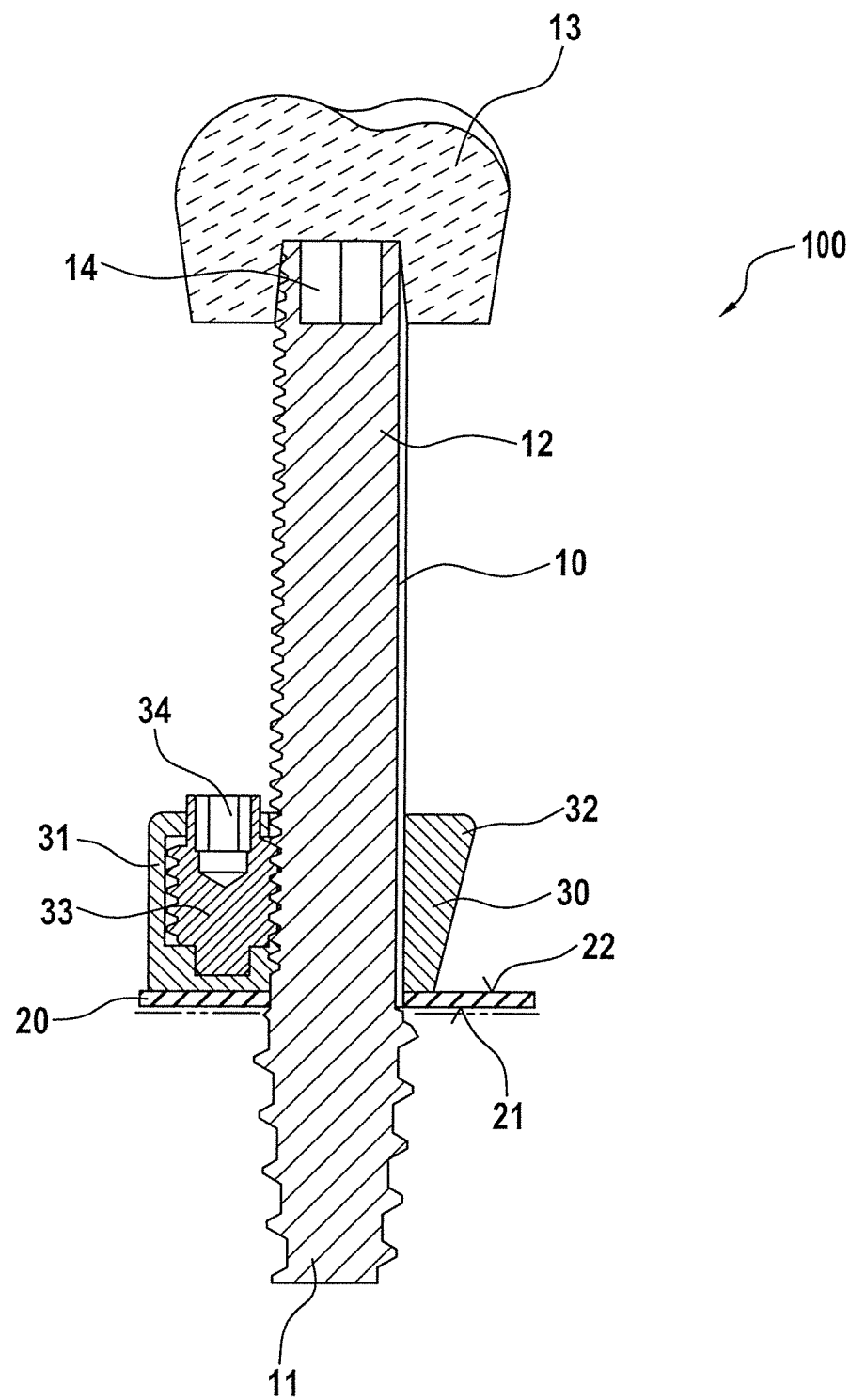

FIG. 4 shows a side view (A) and a cross-section (B) of an alternative embodiment of the implant (100) according to the invention.

It again shows the implant body (10) with apical region (11) and coronal section (12) with toothed rack and hole (14) for attaching a crown, the distraction membrane (20) with contact surface (21), counterface (22), and interconnecting perforations or pores (23), and the connection element (30) with spacer sleeve (32).

In this case, the connection element (30) is designed such that the spacer sleeve (32) forms a housing of a worm gear, in which a threaded body in the form of a worm (33) is rotatably mounted in the spacer sleeve (32) such that the worm (33) and the toothed rack (12) are in active mesh. The rotatory movement of the worm (33) can therefore be transformed into a translational motion of the connection element (30) and thus of the membrane (20) on the toothed rack (12). The worm (33) has a point of application (34) for a tool, for example an Allen wrench, and so the worm (33) can be easily rotated.

Figure 5A:
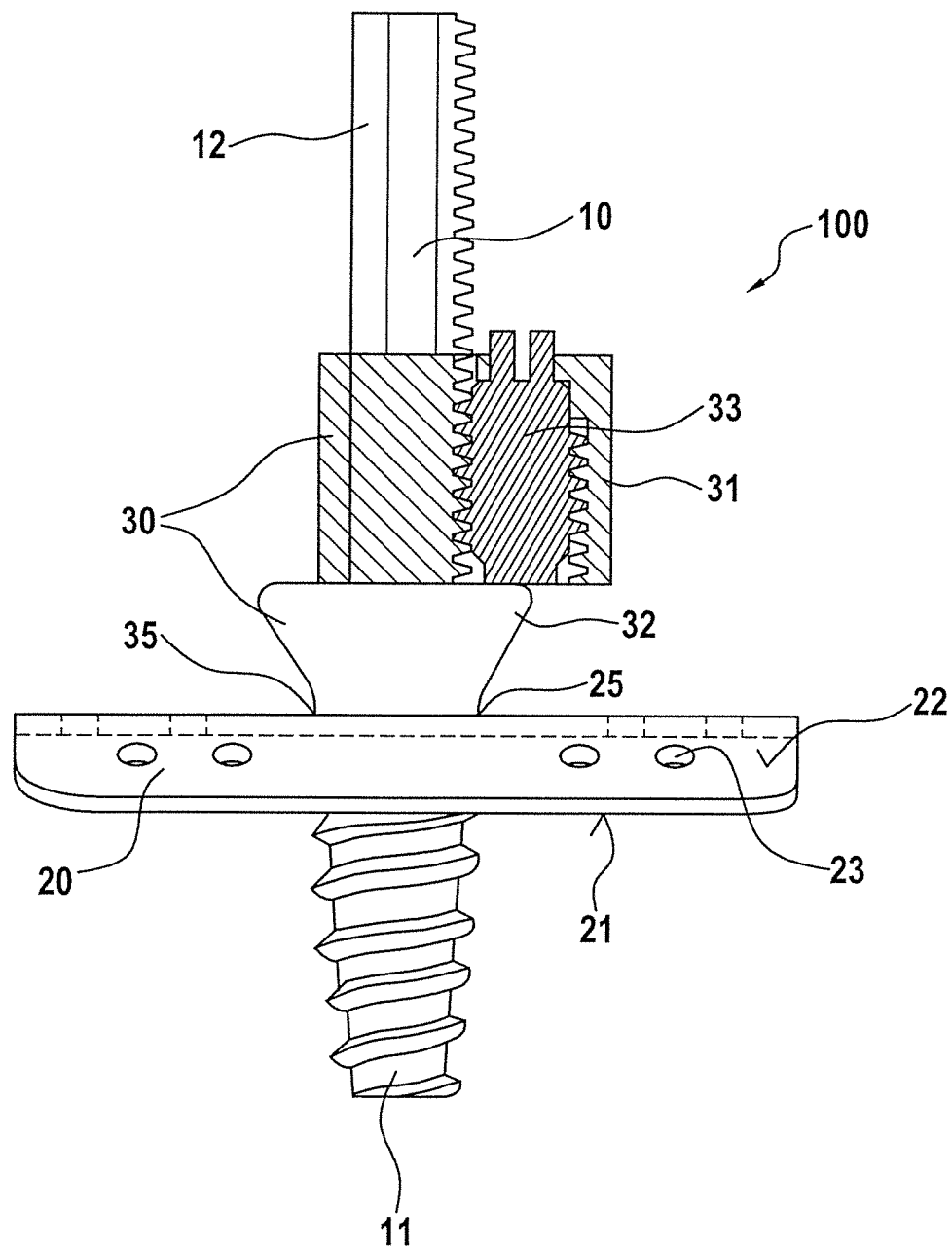
FIG. 5 shows a further alternative embodiment of the implant according to the invention in an assembled state and as individual parts.
Figure 5B:
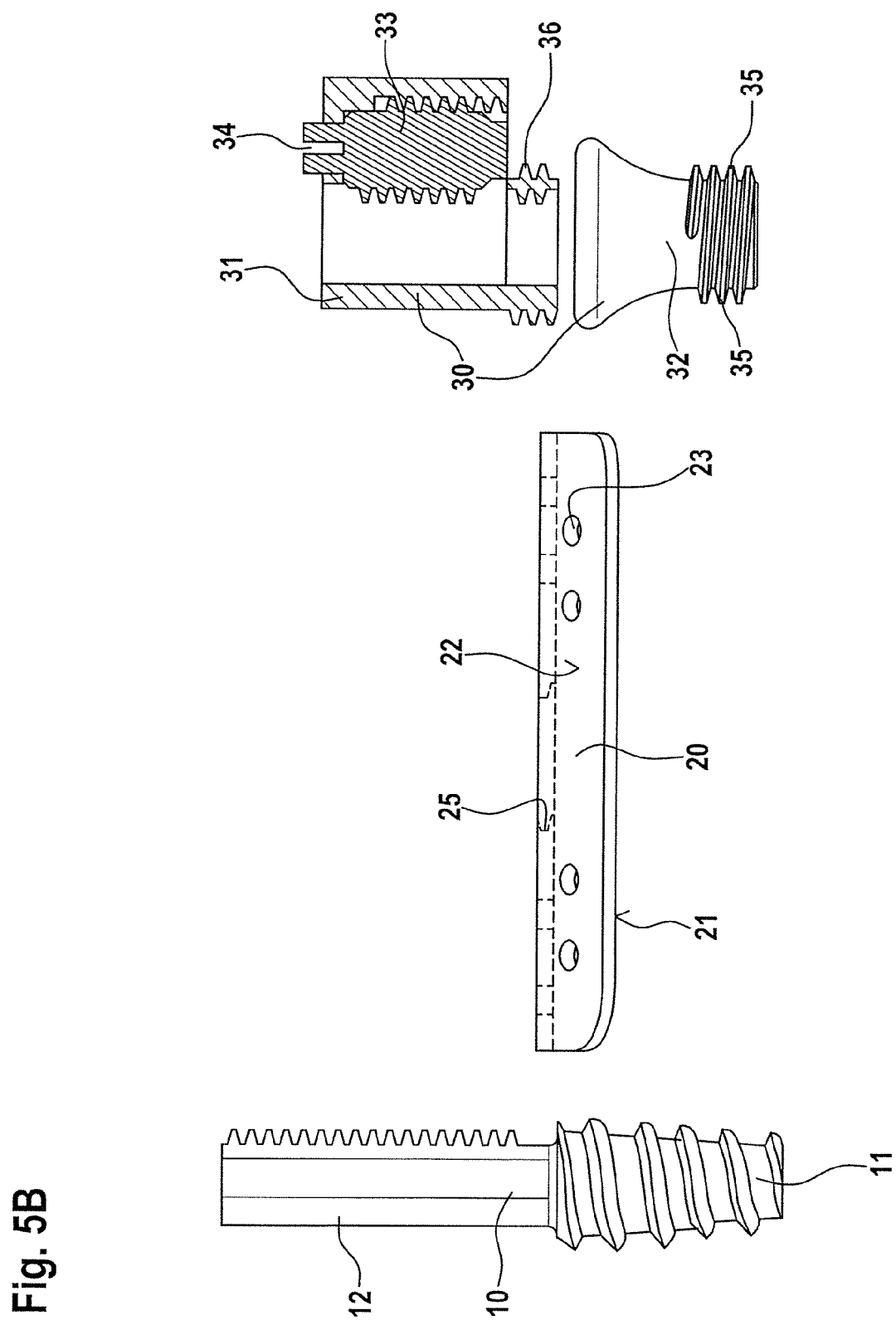

FIG. 5 shows a further alternative embodiment of the implant (100) according to the invention in an assembled state (A) and as individual parts (B).

It again shows the implant body (10) with apical region (11) and coronal section (12) with toothed rack, the distraction membrane (20) with contact surface (21), counterface (22), and interconnecting perforations or pores (23), and the connection element (30).

In this embodiment, the spacer sleeve (32) is screw-connected with (A) or screw-mountable (B) to an external thread (36) of the connection element (30) by means of an internal thread. The membrane is screw-connected with (A) or screw-mountable (B) to an external thread (35) of the spacer sleeve (32) by means of an internal thread in its hole (25).

The connection element (30) is designed such that in the housing (31), a threaded body in the form of a worm (33) in rotatably mounted in the housing (31) such that the worm (33) and the toothed rack (12) are in active mesh. The rotatory movement of the worm (33) can therefore be transformed into a translational motion of the connection element (30) and thus of the membrane (20) on the toothed rack (12). The worm (33) has a point of application (34) for a tool, for example an Allen wrench, and so the worm (33) can be easily rotated.

Figure 6:
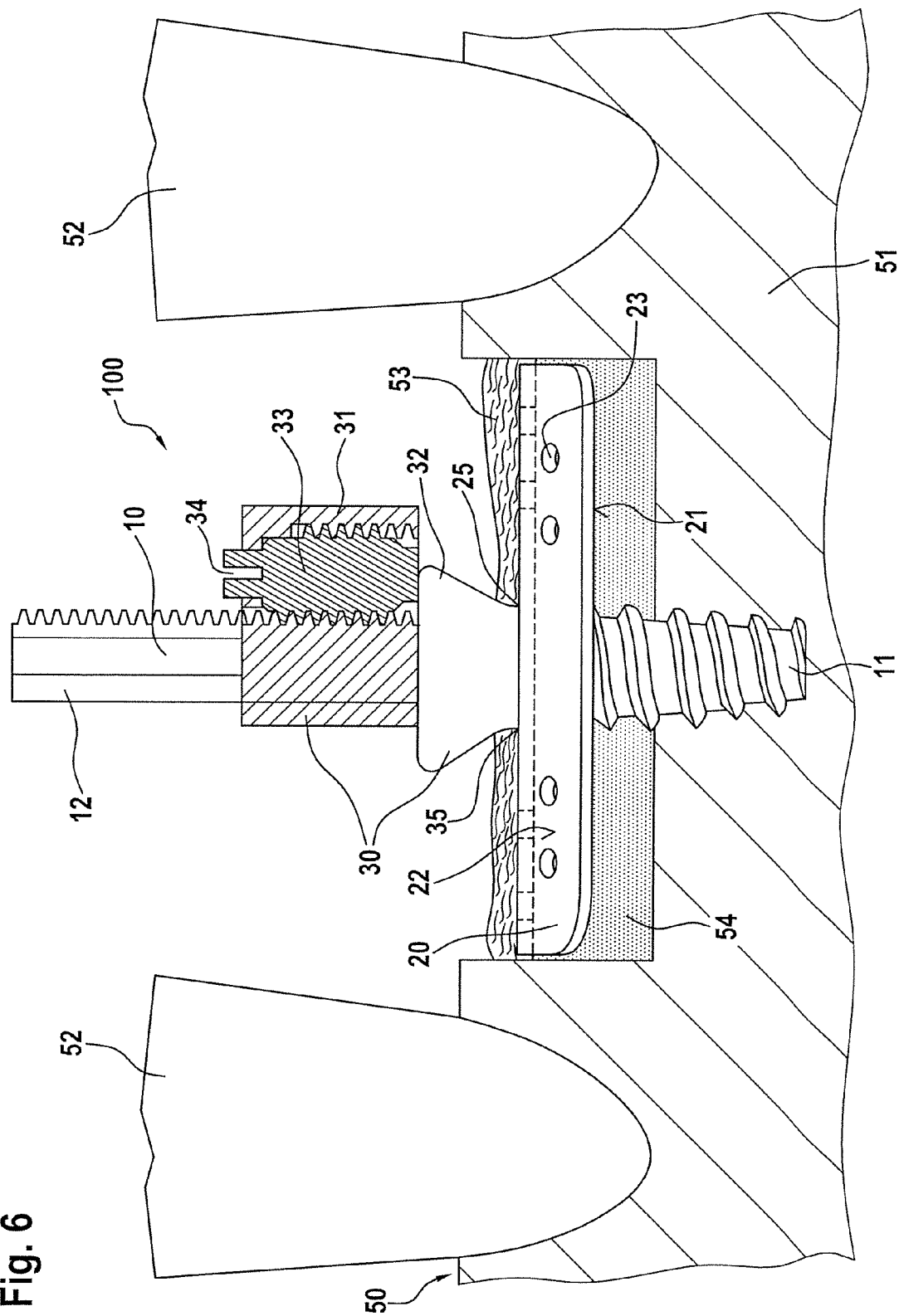
FIG. 6 shows the alternative embodiment of the implant according to the invention from FIG. 5 during a distraction in the jaw region.

FIG. 6 shows the alternative embodiment of the implant (100) according to the invention from FIG. 5 during a distraction in the jaw region (50).

It again shows the implant body (10) with apical region (11) and coronal section (12) with toothed rack, the distraction membrane (20) with contact surface (21), counterface (22), and interconnecting perforations or pores (23), and the connection element (30) with spacer sleeve (32), housing (31), worm (33), and point of application (34). The membrane (20) is screw-connected to an external thread (35) of the spacer sleeve (32) by means of an internal thread in its hole (25).

Furthermore, a jaw bone (51) with two teeth (52) is shown.

The jaw bone (51) has a bone defect, into which the apical part (11) of the implant body (10) is screwed.

With this structure, a method for bone build-up according to the invention is possible.

The membrane (20) is removed from the bone defect at a speed from 0.2 to 2.5 mm per day by means of the connection element (30) by turning the worm (33) daily or every half-day by means of a tool which applies to the point of application (34).

This results in distraction pulses in the tissue (54), particularly callus, which bears against the contact surface (21), said pulses triggering a bone formation. Connective tissue (53) lies above the membrane (20).

Due to the interconnecting perforations or pores (23) of the membrane (20), a material and blood exchange between the tissue (54) which bears against the contact surface (21) and the tissue (53) which bears against the counterface (22) is possible.

Figure 7:
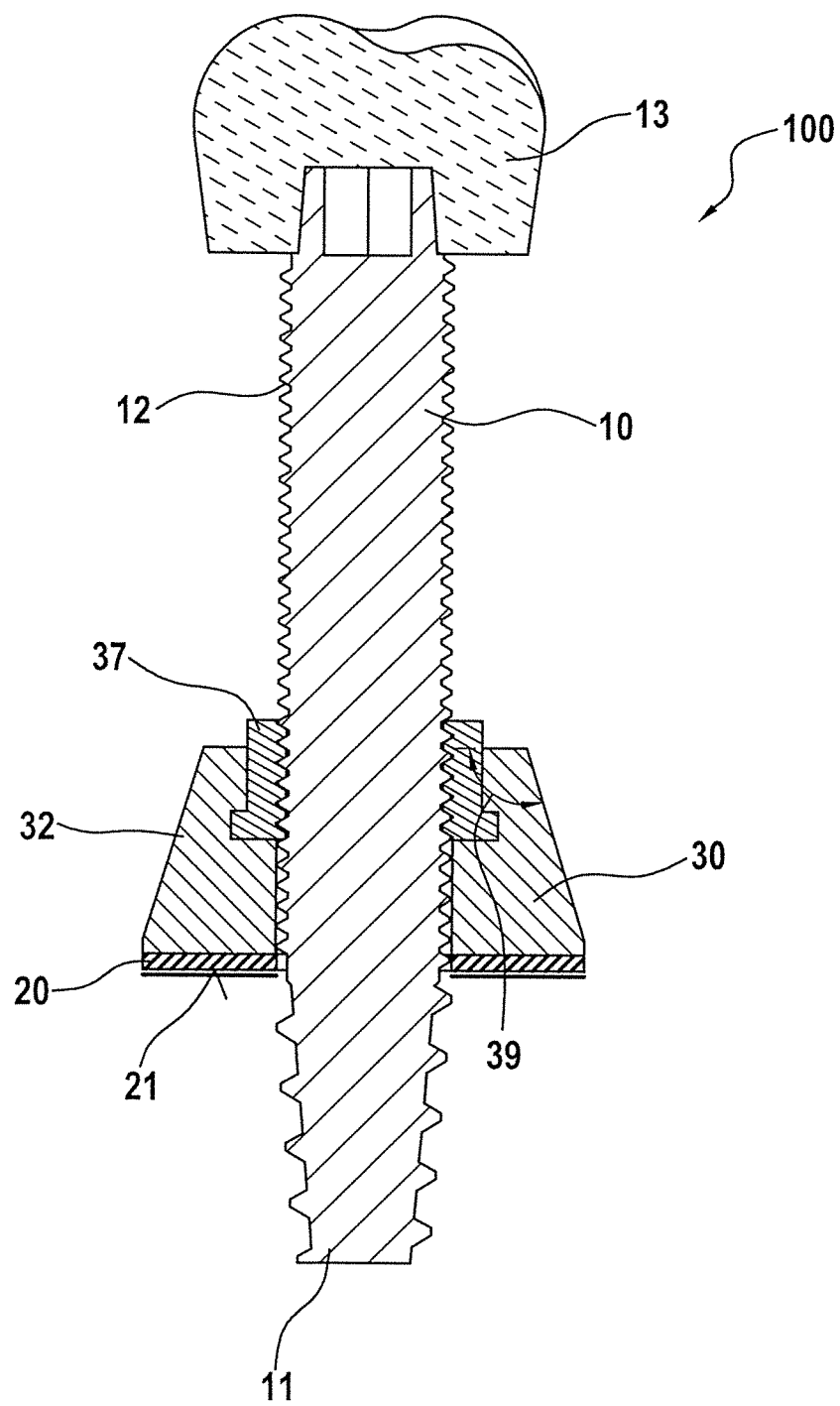
FIG. 7 shows a further alternative embodiment of the implant according to the invention.

FIG. 7 shows a further alternative embodiment of an implant (100) according to the invention.

It again shows the implant body (10) with apical region (11) and coronal section (12) with toothed rack and hole (14) with a crown (13) attached to it.

In this embodiment, the distraction membrane (20) is directly attached with its counterface to the connection element (30) which is designed as a conical spacer sleeve (32). Alternatively, the base surface of the conical spacer sleeve (32) can also be designed as membrane. The contact surface (21) is formed by a layer made from a mineral material.

The connection element (30) with spacer sleeve (32) is again moved along the implant body by means of a rotatably mounted threaded body which is designed as adjusting nut (37).

The size of the base surface of the conical spacer sleeve (32) can advantageously be adjusted by means of the angle (39), and so different spacer sleeves (32) with different base surface size can be used which, however, have the same height and thus correspond in their dimensioning to the length of the implant body (10).

In this case, the membrane (20) is designed so as to be bioresorbable. The membrane (20) can be connected to the spacer sleeve (32) by means of a clamping fit since the cone of the spacer sleeve increases in the direction of the tip (11) of the implant body (10). The completion of the distraction, i.e. after a relatively short period of weeks, is followed by the consolidation period, i.e. a relatively long period of months, during which the bioresorbable membrane, due to progressive resorption, particularly on the edges of the membrane, is no longer held by the conical spacer sleeve, and the spacer sleeve can be removed without problems.

The invention claimed is:

1. An implant comprising:
an implant body; and
a distraction membrane,
wherein the distraction membrane is connected to the implant body by a connection element, the connection element arranged movably at least over a portion of a longitudinal axis of the implant body such that the distraction membrane is slidable along at least a portion of the longitudinal axis of the implant body.

2. The implant according to claim 1, wherein an apical region of the implant body has a thread for screwing the implant body into a bone.

3. The implant according to claim 1, wherein the implant is a tooth implant.

4. The implant according to claim 3, wherein the tooth implant is a temporary implant, preferably a thread cutter.

5. The implant according to claim 1, wherein the distraction membrane has a hole through which the implant body extends.

6. The according to claim 1, wherein the connection element comprises a self-locking transmission for moving the distraction membrane along the longitudinal axis of the implant body.

7. The implant according to claim 5, wherein the hole in the distraction membrane has an internal thread and the connection element has an external thread, wherein the external thread of the connection element can be screwed into the internal thread of the distraction membrane.

8. The implant according to claim 5, wherein the distraction membrane is connected to the connection element by an interconnection selected from a group consisting of a tongue and groove connection and a click connection.

9. The implant according to claim 1, wherein the connection element has a spacer sleeve.

10. The implant according to claim 1, wherein the implant body, along the longitudinal axis, has a lower portion with a thread, and a second portion above the lower portion, wherein the second portion is designed as a toothed rack.

11. The implant according to claim 10, wherein the connection element has a housing with a passage and a threaded body, wherein the toothed rack is inserted in longitudinal extension through the passage essentially without play through the housing, and wherein the threaded body is rotatably mounted in the housing such that the threaded body and the toothed rack are in active mesh.

12. The implant according to claim 11, wherein the housing is designed as a spacer sleeve.

13. The implant according to claim 12, wherein the connection element has a spacer sleeve and a housing, wherein the housing has an external thread on one end, and wherein the spacer sleeve is, at least to some extent, conical, and wherein the spacer sleeve has, on the first end with the smaller diameter, an external thread for screwing into the internal thread of the membrane, and wherein the spacer sleeve, on the second end that is opposite the first end, has an internal thread, into which the external thread of the housing can be screwed.

14. The implant according to claim 9, wherein the connection element is designed as a spacer sleeve, and wherein the membrane is attached to a surface of the spacer sleeve.

15. The implant according to claim 9, wherein the connection element is designed as a spacer sleeve, and wherein the membrane is formed by a surface of the spacer sleeve.

16. The implant according to claim 1, further comprising a crown.

17. The implant according to claim 1, wherein the implant body is made of a resorbable material, zircon, or a metal.

18. The implant according to claim 1, wherein the distraction membrane is curved.

19. The implant according to claim 1, wherein the distraction member includes an upper surface directly attached to the connection element and the distraction membrane radially extends out from the implant body beyond the connection element.

20. An implant comprising:
an implant body extending in a longitudinal direction;
a connection element circumferentially surrounding the implant body and linearly movable along the implant body;
an adjustment member circumferentially surrounding the implant body and rotatable relative to the implant body; and
a distraction membrane, the distraction member including an upper surface directly attached to the connection element and the distraction membrane radially extending out from the implant body beyond the connection element,
wherein the distraction membrane and the connection element are collectively movable along at least a portion of the longitudinal axis of the implant body.

* * * * *